US010415677B2

(12) United States Patent
Horn

(10) Patent No.: US 10,415,677 B2
(45) Date of Patent: Sep. 17, 2019

(54) TWO-STAGE TELESCOPIC SPINDLE DRIVE

(71) Applicant: LAKEVIEW INNOVATION LTD., Buochs (CH)

(72) Inventor: Carsten Horn, Ettenheim (DE)

(73) Assignee: LAKEVIEW INNOVATION LTD., Buochs (CH)

( * ) Notice: Subject to any disclaimer, the term of this patent is extended or adjusted under 35 U.S.C. 154(b) by 0 days.

(21) Appl. No.: 15/794,878

(22) Filed: Oct. 26, 2017

(65) Prior Publication Data

US 2018/0119783 A1    May 3, 2018

(30) Foreign Application Priority Data

Oct. 28, 2016 (EP) .................................. 16196318

(51) Int. Cl.
*F16H 25/20* (2006.01)
*A61M 5/315* (2006.01)

(52) U.S. Cl.
CPC ......... *F16H 25/2056* (2013.01); *A61M 5/315* (2013.01); *A61M 5/31578* (2013.01); *A61M 2005/31598* (2013.01); *F16H 2025/204* (2013.01); *F16H 2025/2081* (2013.01)

(58) Field of Classification Search
CPC .. F16H 25/18; F16H 25/2056; F16H 25/2053; F16H 25/2059; F16H 2025/2081
USPC ...................................................... 74/89.35
See application file for complete search history.

(56) References Cited

U.S. PATENT DOCUMENTS

| 1,862,759 A | * | 6/1932 | Morrison | .................. B66F 3/10 |
| | | | | 254/102 |
| 3,404,580 A | * | 10/1968 | Valenti | ................ F16H 25/2056 |
| | | | | 74/89.35 |
| 3,576,135 A | * | 4/1971 | Tschunko | ................ F16H 25/20 |
| | | | | 74/89.24 |
| 4,521,707 A | * | 6/1985 | Baker | ..................... F16H 25/20 |
| | | | | 310/112 |
| 4,651,581 A | * | 3/1987 | Svensson | .................. B66F 3/10 |
| | | | | 74/89.35 |

(Continued)

FOREIGN PATENT DOCUMENTS

DE    197 17 107 A1    11/1998
WO    WO 2011/006925 A1    1/2011

(Continued)

OTHER PUBLICATIONS

European Search Report dated Apr. 28, 2017 for European Application No. 16196318.

*Primary Examiner* — Jake Cook
*Assistant Examiner* — T. Scott Fix
(74) *Attorney, Agent, or Firm* — Buchanan Ingersoll & Rooney PC

(57) ABSTRACT

The present disclosure relates to a telescopic spindle drive having a first telescope element, a second telescope element which is extensible in relation to the first telescope element along an axis of the telescopic spindle drive, and a third telescope element which is extensible in relation to the second telescope element along the axis. A drive includes a rotatively driven first drive element which is supported rotatably and axially unshiftably in relation to the first telescope element. The drive also includes a rotatively driven second drive element which is also rotatably supported in relation to the first telescope element.

19 Claims, 2 Drawing Sheets

(56) References Cited

U.S. PATENT DOCUMENTS

| | | | | |
|---|---|---|---|---|
| 4,893,704 | A * | 1/1990 | Fry | E05B 81/25 |
| | | | | 192/141 |
| 5,035,094 | A * | 7/1991 | Legare | B63B 15/0083 |
| | | | | 343/903 |
| 5,129,273 | A * | 7/1992 | Fukui | F16H 25/2018 |
| | | | | 74/89.35 |
| 5,937,699 | A * | 8/1999 | Garrec | B25J 18/025 |
| | | | | 74/89.35 |
| 6,067,868 | A * | 5/2000 | Nakamura | F16H 25/20 |
| | | | | 74/89.35 |
| 7,066,909 | B1 | 6/2006 | Peter et al. | |
| 2004/0000818 | A1 | 1/2004 | Preuthun et al. | |
| 2006/0096399 | A1 * | 5/2006 | Harper | F16H 25/24 |
| | | | | 74/424.71 |
| 2010/0018334 | A1 | 1/2010 | Lessing | |
| 2010/0192715 | A1 * | 8/2010 | Vauchel | F02K 1/763 |
| | | | | 74/89.35 |
| 2012/0220941 | A1 | 8/2012 | Jones | |
| 2014/0290403 | A1 | 10/2014 | Wu | |
| 2016/0047446 | A1 * | 2/2016 | Hung | F16H 25/2056 |
| | | | | 74/89.35 |
| 2017/0009858 | A1 * | 1/2017 | Klode | F16D 65/16 |
| 2017/0056579 | A1 | 3/2017 | Müri | |
| 2017/0056582 | A1 | 3/2017 | Niklaus | |
| 2017/0175859 | A1 * | 6/2017 | Brockmeier | A61M 5/31511 |

FOREIGN PATENT DOCUMENTS

| | | |
|---|---|---|
| WO | WO 2015/172828 A1 | 11/2015 |
| WO | WO 2015/172962 A1 | 11/2015 |

* cited by examiner

TWO-STAGE TELESCOPIC SPINDLE DRIVE

The present invention refers to a telescopic spindle drive.

A generic telescopic spindle drive comprises a first telescope element, a second telescope element which is extensible in relation to the first telescope element along an axis of the telescopic spindle drive, and a third telescope element which is extensible in relation to the second telescope element along the axis. The drive of the telescopic spindle drive comprises a rotatively driven first drive element which is supported rotatably and axially unshiftably in relation to the first telescope element. A thread of the first drive element and a first thread of the second telescope element which is in engagement therewith jointly form a first spindle drive. A second thread of the second telescope element and a thread of the third telescope element which is in engagement therewith jointly form a second spindle drive.

Telescopic spindle drives are for instance used in medical technology in medicament dosage systems or injection devices. These are normally small, portable, battery-operated hand-held devices. A standard telescopic spindle drive for such applications is for instance described in WO201106925 A1. A telescopic spindle drive of the generic type according to the preamble of the independent claim 1 is described in DE 19717107 A1. In this telescopic spindle drive the second telescope element is either rotatively driven in response to the frictional forces acting on the second telescope element or is shifted by the first spindle drive along the axis of the telescopic spindle drive. The movement of the second telescope element may also be a composed shifting/rotational movement. If the second telescope element is shifted, it will entrain the third telescope element. As the second telescope element is rotated, the rotational movement produces an advance movement of the third telescope element via the second spindle drive.

In the aforementioned uses of known telescopic spindle drives it primarily matters with respect to user convenience that the lifetime of the device in which the telescopic spindle drive is used is as long as possible. At the same time the drives should also be fast and efficient.

It is the object of the present invention to develop the telescopic spindle drive of the generic type in an advantageous manner, thereby increasing efficiency.

In a telescopic spindle drive the object is achieved according to the invention whenever the drive of the telescopic spindle drive comprises a rotatively driven second drive element which is also rotatably supported in relation to the first telescope element, wherein a rotatively driving engagement exists between the second drive element and the second telescope element, and wherein the second telescope element is shiftable in axial direction in relation to the second drive element.

In comparison with the telescopic spindle drive known from DE 19717107 A1 the solution according to the invention has the advantage that it no longer depends on the operative frictional forces whether the second telescope element is just co-rotated or axially shifted. The advance speed of both the second telescope element and the third telescope element can be adjusted by way of the speed difference of the rotational speeds of the first and second drive element. The drive can thereby be optimized on the whole also with respect to the operative frictional forces.

The telescopic spindle drive may comprise a base which is either fixedly connected to the first telescope element or forms the first telescope element itself. Both drive elements are preferably rotatably supported on the base.

Advantageous embodiments of the present invention are the subject of the sub-claims.

According to a particularly preferred embodiment of the present invention the drive of the telescopic spindle drive is configured such that the rotational speed of the first drive element is twice the rotational speed of the second drive element. Preferably, the first drive element and the second drive element have the same rotational direction. The axial speed of the third telescope element is in this embodiment twice the axial speed of the second telescope element. With a uniform thread pitch of the engaging threads the third telescope element covers twice the distance in comparison with the second telescope element. This has the consequence that all thread components move relative to one another only at the single drive speed which corresponds to the rotational speed of the second drive element. This minimizes friction and optimizes efficiency. Likewise, the required torque is thereby optimally adjusted. Furthermore, the service life of the telescopic spindle drive is improved thereby, and great axial forces are achievable.

Of course, it is also possible to choose a different ratio for the ratio of the rotational speeds of the first and second drive element. It is however within the meaning of the present invention that the first drive element is driven at a speed different from that of the second drive element.

By way of alternative combinations of the rotational speeds of the two drive elements and due to different thread pitches and thread lengths the telescopic spindle drive can be variably adapted to special requirements.

According to a further, particularly preferred embodiment of the present invention the first drive element and the second drive element are supported coaxially to each other and each time coaxially to the axis of the telescopic spindle drive rotatably and axially unshiftably in relation to the first telescope element. This embodiment ensures a particularly compact construction. It is here of special advantage when the first drive element comprises a first pinion, wherein the second drive element comprises a second pinion, and wherein first and second drive elements are drivable via first and second pinions by means of a spur gear of the telescopic spindle drive by a single electric motor. This results not only in a compact, but also in a particularly inexpensive construction. The ratio of the drive speeds of the first and second drive element is invariably fixed by the spur gear. The electric motor is preferably also part of the telescopic spindle drive according to the invention. In an alternative embodiment it is also conceivable to drive the two drive elements each time separately by means of two independent electric motors. The speed difference between the two drive elements can thereby be adjusted individually or can also be controlled.

According to a further, particularly preferred embodiment of the present invention, the first drive element and the second drive element are designed as two sleeves inserted into each other. Here, the first drive element preferably encloses the second drive element. This embodiment is also conducive to a compact construction of the telescopic spindle drive according to the invention. It is here of special advantage when the second telescope element comprises an outer sleeve and a middle extension which is enclosed by the outer sleeve of the second telescope element and firmly connected to said sleeve, wherein first and second drive element dip into a space between the outer sleeve of the second telescope element and the middle extension, wherein the thread of the first drive element is an external thread, and wherein the first thread of the second telescope element is an internal thread formed on an inside of the outer sleeve of the second telescope element. The middle extension of the second telescope element may for instance have a 4-cornered cross section and may be guided in an axially shiftable manner in an also 4-cornered recess of the second drive element. This results in a simple anti-twist protection between the second telescope element and the second drive element. Of course alternative cross-sections which ensure a corresponding form closure for axial guidance are also possible.

According to a further preferred embodiment of the present invention the second thread of the second telescope element is an external thread which is formed on an outside of the outer sleeve of the second telescope element. This external thread cooperates with a corresponding internal thread of the third telescope element.

According to a further preferred embodiment of the present invention the third telescope element is designed as a plunger sleeve.

According to a further, particularly preferred embodiment of the present invention the third telescope element is secured against rotation with respect to the first telescope element. Here, the first telescope element is further preferably designed as a fixed sleeve, wherein the telescopic spindle drive further comprises a middle sleeve which encloses the second telescope element at least partially radially and is shiftably supported in relation to the first telescope element, which is designed as a fixed sleeve, along the axis of the telescopic spindle drive, wherein the third telescope element is also designed as a sleeve and is shiftably supported in relation to the middle sleeve along the axis of the telescopic spindle drive, and wherein an anti-twist protection exists between the first telescope element and the middle sleeve and also between the middle sleeve and the third telescope element. The anti-twist protection is further preferably implemented by means of at least one pin which is formed on a sleeve and is axially guided in a guide slot or a guide groove of the respective other sleeve. All of the three sleeves, namely the first telescope element, the middle sleeve and the third telescope element, are arranged coaxially to each other and dip into one another.

In a further preferred embodiment of the present invention the first telescope element is the outermost telescope element of the telescopic spindle drive and has an outer diameter of less than 50 mm, preferably less than 25 mm.

All components of the spindle mechanism consist preferably of metal and/or ceramic. Specifically, all components of the telescopic spindle drive that have a thread are preferably made from a surface-polished ceramic, particularly a zirconium- or aluminum-oxide ceramic. The telescopic spindle drive according to the invention is thereby particularly inexpensive and has a long lifetime.

An embodiment of the present invention will now be explained in more detail with reference to drawings.

As for the following explanations, like parts are designated by like reference numerals. If a figure contains reference numerals which are not discussed in more detail in the associated description of the figures, reference will be made to preceding or succeeding descriptions of the figures.

Figure 1:
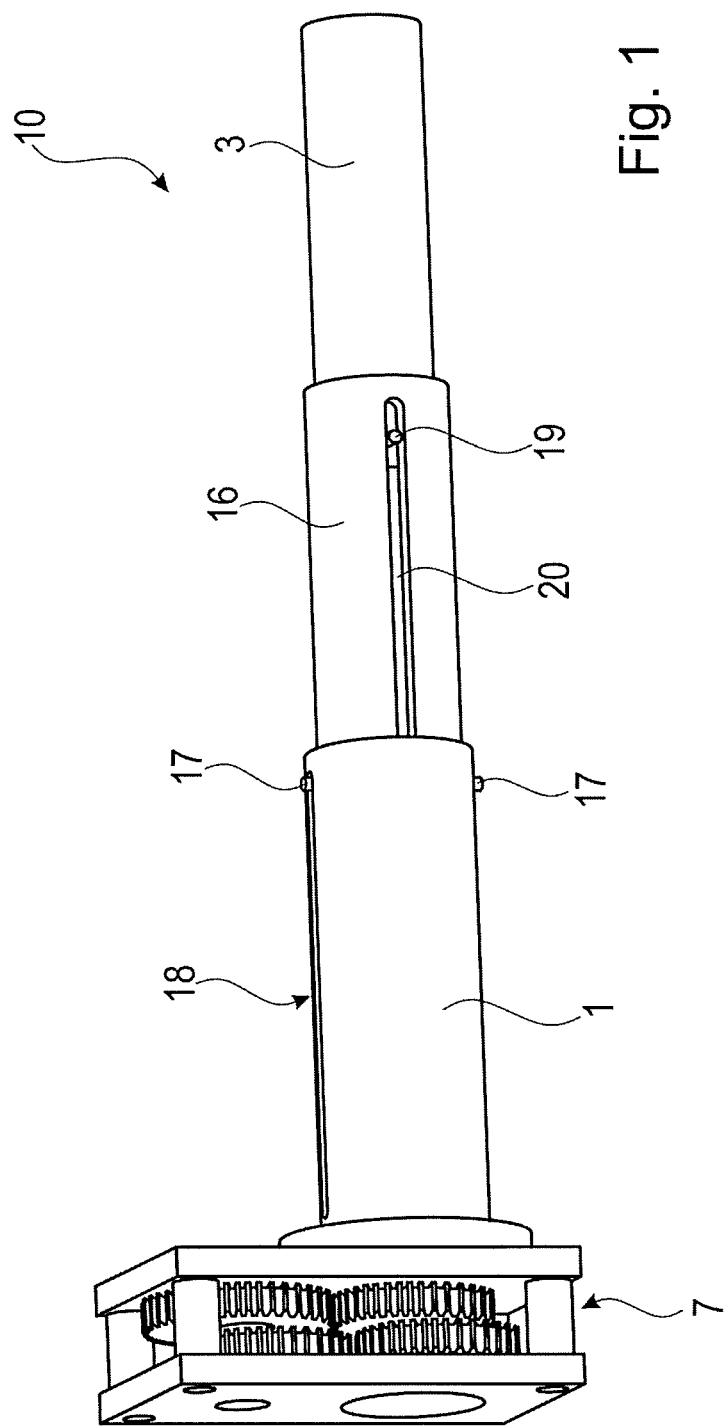
FIG. 1 shows an embodiment of a telescopic spindle drive according to the invention in a side view.

FIG. 1 shows an embodiment of the telescopic spindle drive 10 according to the invention in a side view. The illustration shows the telescopic spindle drive in the maximally extended position. The fixed base 7, the first telescope element 1 which is fixedly connected to the base, and the completely extended third telescope element 3 of the telescopic spindle drive according to the invention are visible. By contrast, the second telescope element 2 is just shown in the sectional representation of FIG. 2. In FIG. 1 it is concealed by a middle sleeve 16 which is arranged between the first telescope element and the third telescope element. The middle sleeve 16 primarily serves as an anti-twist protection for the third telescope element. For this purpose the third telescope element 3 comprises two pins 19 that are axially guided in corresponding longitudinal slots 20 of the middle sleeve and secure the third telescope element against rotation in relation to the middle sleeve. Likewise, the middle sleeve also comprises two pins 17 that are axially guided in corresponding longitudinal slots 18 of the first telescope element 1 and secure the middle sleeve in relation to the first telescope element against rotation. The first telescope element and the third telescope element are, just like the middle sleeve 16, equally formed as sleeves, so that the components 1, 16 and 3 are inserted into one another in the manner of a telescope and dip into one another when the telescopic spindle drive according to the invention is retracted.

Figure 2:
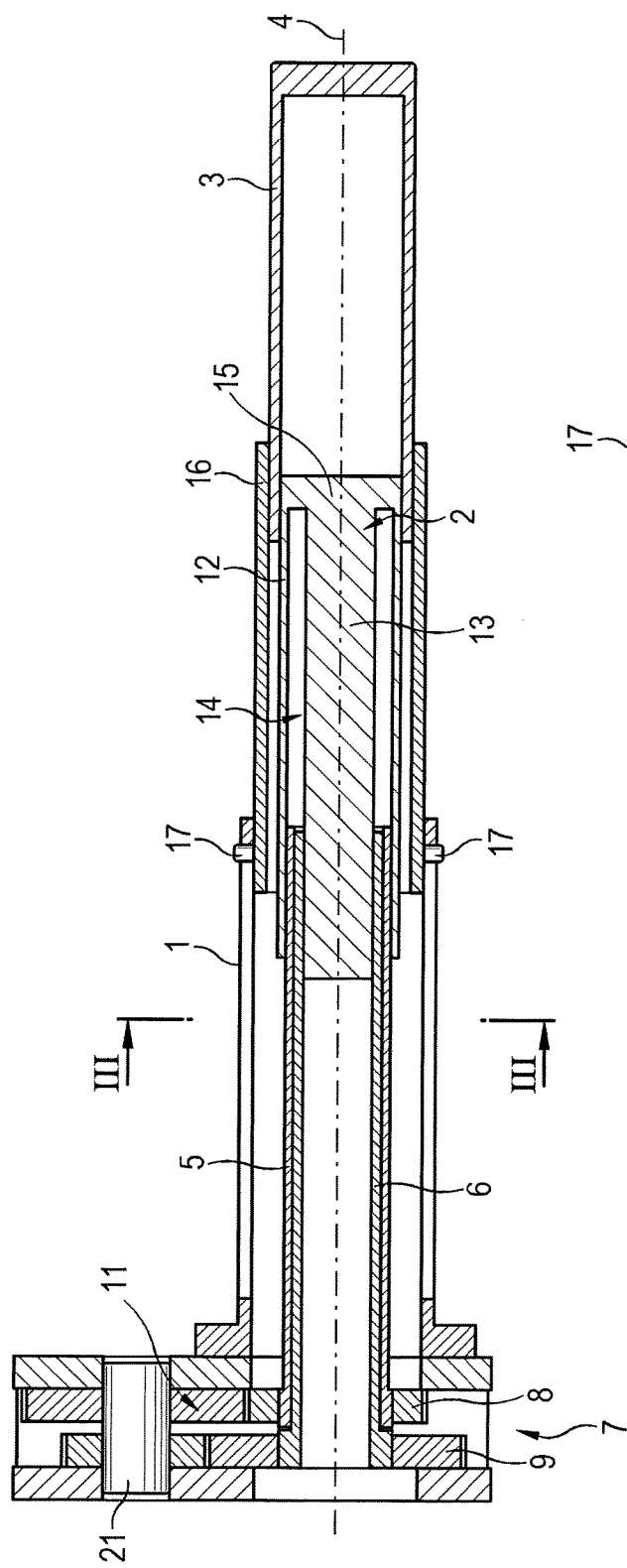
FIG. 2 is a longitudinal section of the telescopic spindle drive according to the invention from FIG. 1.

The longitudinal section of FIG. 2 shows the mechanical inner workings of the telescopic spindle drive 10 according to the invention. First of all it can be seen that the already aforementioned components 1, 16 and 3 are arranged coaxially with respect to the axis 4 of the telescopic spindle drive according to the invention. Furthermore, two drive elements 5 and 6 are also coaxially arranged with respect to the axis 4. The drive elements 5 and 6 are supported rotatably and axially unshiftably in the base 7 of the telescopic spindle drive according to the invention. Both drive elements are designed as sleeves, wherein the first drive element 5 radially encloses the second drive element 6. The telescopic spindle drive has a drive section which is mounted on the base 7 and comprises in the illustrated embodiment a spur gear 11 having an input shaft 21 driven by an electric motor (not shown). The spur gear 11 is in engagement with a pinion 8 of the first drive element 5 and also with a pinion 9 of the second drive element 6. The gear ratio is here chosen such that the first drive element 5 rotates twice as fast as the second drive element 6.

Both drive elements 5 and 6 are in engagement with the second telescope element 2 of the telescopic spindle drive according to the invention. This element consists of an outer sleeve 12 and an extension 13 which is enclosed by the outer sleeve 12 and is connected firmly or also integrally to the outer sleeve 12 via the head end 15 of the second telescope element. An annular space 14 which accommodates the sleeve-like first drive element 5 and also the sleeve-like second drive element 6 enclosed by said first drive element exists between the outer sleeve 12 and the middle extension 13. The drive elements 5 and 6 dip all the more into the space 14 the more the telescopic spindle drive according to the invention is retracted. The first drive element has an external thread which is in engagement with an internal thread formed on the inside of the outer sleeve 12 of the second telescope element 2. The external thread of the first drive element and the internal thread on the inside of the outer sleeve 12 jointly form a first spindle drive of the telescopic spindle drive according to the invention. Likewise, the second telescope element 2 has an external thread which is formed on the outside of the outer sleeve 12 and is in engagement with a corresponding internal thread of the third telescope element 3. The external thread of the second telescope element and the internal thread of the third telescope element jointly form a second spindle drive of the telescopic spindle drive according to the invention.

Figure 3:
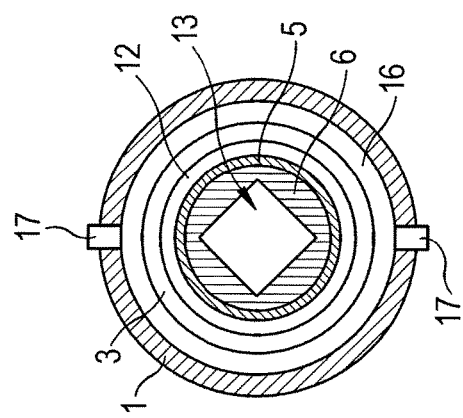
FIG. 3 shows the telescopic spindle drive according to the invention from FIGS. 1 and 2 in cross section along the section line III drawn in FIG. 2.

As becomes particularly apparent from FIG. 3, there is a form closure between the extension 13 of the second telescope element 2 and a corresponding recess of the second drive element, said form closure ensuring that the second telescope element 2 is co-rotating with the second drive element 6. The second telescope element 2, however, is axially shiftable in relation to the second drive element 6. For this purpose the extension 13 of the second telescope element has a 4-cornered cross section; the recess in the second drive element 6 is also 4-cornered in a corresponding manner. Of course, other cross sections are conceivable that ensure a form closure between the two components and simultaneously allow an axial movement of the second telescope element 2 in relation to the second drive element 6.

In this embodiment the threads (not shown) of the components in question are all given the same pitch and the same rotational direction. Since the first drive element 5 rotates approximately twice as fast as the second drive element 6, an advance movement of the third telescope element which is twice the advance movement of the second telescope element is generated owing to the anti-twist protection of the third telescope element with respect to the first telescope element. Here, the relative rotational speed of all thread components to one another corresponds to the single drive speed of the second drive element, whereby the efficiency of the telescopic spindle drive according to the invention is optimized.

The invention claimed is:

1. A telescopic spindle drive comprising:
   a first telescope element;
   a second telescope element which is extensible in relation to the first telescope element along an axis of the telescopic spindle drive;
   a third telescope element which is extensible in relation to the second telescope element along the axis; and
   a drive of the telescopic spindle drive having a rotatively driven first drive element which is supported rotatably and axially unshiftably in relation to the first telescope element, wherein a thread of the first drive element and a first thread of the second telescope element which is in engagement therewith jointly form a first spindle drive, and wherein a second thread of the second telescope element and a thread of the third telescope element which is in engagement therewith jointly form a second spindle drive, wherein the drive of the telescopic spindle drive includes a rotatively driven second drive element which is also rotatably supported in relation to the first telescope element, wherein a rotatively driving engagement exists between the second drive element and the second telescope element, the second telescope element is shiftable in axial direction in relation to the second drive element:
   wherein the second telescope element comprises:
   an outer sleeve and a middle extension which is enclosed by the outer sleeve of the second telescope element and is connected thereto, wherein first and second drive elements dip into a space between the outer sleeve of the second telescope element and the middle extension, wherein the thread of the first drive element is an external thread, and wherein the first thread of the second telescope element is an internal thread which is formed on an inside of the outer sleeve of the second telescope element.

2. Telescopic spindle drive according to claim 1, wherein the drive is configured such that a rotational speed of the first drive element will be twice a rotational speed of the second drive element.

3. Telescopic spindle drive according to claim 1 wherein the first drive element and the second drive element are supported coaxially to each other and coaxially to the axis of the telescopic spindle drive rotatably and axially unshiftably in relation to the first telescope element.

4. Telescopic spindle drive according to claim 3, wherein the first drive element comprises:
   a first pinion, wherein the second drive element comprises:
   a second pinion, and wherein first and second drive element are drivable via first and second pinion via a spur gear of the telescopic spindle drive by a single electric motor.

5. Telescopic spindle drive according to claim 1, wherein first drive element and second drive element are designed as two sleeves, one of the first and second drive elements being inserted into the other of the first and second drive elements.

6. Telescopic spindle drive according to claim 1, wherein the second thread of the second telescope element is an external thread which is formed on an outside of the outer sleeve of the second telescope element.

7. Telescopic spindle drive according to claim 1, wherein the third telescope element is a plunger sleeve.

8. Telescopic spindle drive according to claim 1, wherein the third telescope element is configured to be secured against rotation with respect to the first telescope element.

9. Telescopic spindle drive according to claim 8, wherein the first telescope element is configured as a fixed sleeve, and wherein the telescopic spindle drive comprises:
   a middle sleeve which encloses the second telescope element at least partially radially and is shiftably supported with respect to the first telescope element, which is configured as a fixed sleeve, along the axis of the telescopic spindle drive, wherein the third telescope element is configured as a sleeve and is shiftably supported with respect to the middle sleeve along the axis of the telescopic spindle drive, and wherein an anti-twist protection is included between the first telescope element and the middle sleeve and also between the middle sleeve and the third telescope element.

10. Telescopic spindle drive according to claim 1, wherein the first telescope element is the outermost telescope element of the telescopic spindle drive and has an outer diameter of less than 50 mm.

11. Telescopic spindle drive according to claim 1, wherein all components of the telescopic spindle drive that have a thread are made from a surface-polished ceramic.

12. Telescopic spindle drive according to claim 1, wherein the first telescope element is the outermost telescope element of the telescopic spindle drive and has an outer diameter of less than 25 mm.

13. Telescopic spindle drive according to claim 1, wherein all components of the telescopic spindle drive that have a thread are made from at least of zirconium- or aluminum-oxide ceramic.

14. Telescopic spindle drive according to claim 2, wherein the first drive element and the second drive element are supported coaxially to each other and coaxially to the axis of the telescopic spindle drive rotatably and axially unshiftably in relation to the first telescope element.

15. Telescopic spindle drive according to claim 14, wherein the first drive element and the second drive element are designed as two sleeves, one of the first and second drive elements being inserted into the other of the first and second drive elements.

16. Telescopic spindle drive according to claim 15, wherein the third telescope element is a plunger sleeve.

17. Telescopic spindle drive according to claim 16, wherein the third telescope element is configured to be secured against rotation with respect to the first telescope element.

18. Telescopic spindle drive according to claim 17, wherein the first telescope element is the outermost telescope element of the telescopic spindle drive and has an outer diameter of less than 50 mm.

19. Telescopic spindle drive according to claim 18, wherein all components of the telescopic spindle drive that have a thread are made from a surface-polished ceramic.

* * * * *